United States Patent
Horie

(10) Patent No.: US 6,862,095 B2
(45) Date of Patent: Mar. 1, 2005

(54) METHOD OF MEASURING DIELECTRIC CONSTANT USING LIGHT IN A PLURALITY OF WAVELENGTH RANGES

(75) Inventor: Masahiro Horie, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 141 days.

(21) Appl. No.: 10/235,648

(22) Filed: Sep. 6, 2002

(65) Prior Publication Data

US 2003/0067603 A1 Apr. 10, 2003

(30) Foreign Application Priority Data

Sep. 21, 2001 (JP) .................... P2001-288534

(51) Int. Cl.⁷ ............................................. G01N 21/55
(52) U.S. Cl. ..................................................... 356/445
(58) Field of Search .......................... 356/72, 73, 319, 356/326, 328, 357, 359, 360, 371, 381, 517, 491, 450, 484, 487, 485, 445, 128; 250/339.07, 339.08

(56) References Cited

U.S. PATENT DOCUMENTS

| | | | |
|---|---|---|---|
| 4,905,170 A | | 2/1990 | Forouhi et al. |
| 5,796,983 A | | 8/1998 | Herzinger et al. |
| 5,872,630 A | | 2/1999 | Johs et al. |
| 5,943,122 A | * | 8/1999 | Holmes ........................ 356/73 |
| 5,999,267 A | * | 12/1999 | Zawaideh ..................... 356/630 |
| 6,210,745 B1 | | 4/2001 | Gaughan et al. |
| 6,556,306 B2 | * | 4/2003 | Jiang et al. .................. 356/517 |

FOREIGN PATENT DOCUMENTS

JP    3285365    8/2002

OTHER PUBLICATIONS

"Reference™ Spectroscopic Ellipsometer for On–Line", Stehle et al., Future FAB International, (2000) p. 250–251.
"Optical Properties of Amorphous and Polycrystalline Tantalum Oxide Thin Films Measured by Spectroscopic Ellipsometry From 0.03 to 8.5Ev", Franke et al., thin solid films 388 (2001) 283–289.
"Determination of Optical Anisotrophy in Calcite From Ultraviolet to Mid–Infrared by Generalized Ellipsometry", Thompson et al., Thin Solid Films, 313–314 (1998)341–346.

(List continued on next page.)

Primary Examiner—Michael P. Stafira
(74) Attorney, Agent, or Firm—McDermott Will & Emery LLP

(57) ABSTRACT

In a dielectric constant measuring apparatus provided are a light source for irradiating a substrate with light in a visible or near-ultraviolet wavelength range, a spectroscope for receiving reflected light from the substrate, and a first optical characteristic acquiring unit for acquiring the spectral reflectance of the substrate. Further are provided therein a light source for irradiating the substrate with light in an infrared wavelength range, a spectroscope for receiving transmission light from the substrate, and a second optical characteristic acquiring unit for acquiring the spectral transmittance of the substrate. The dielectric constant of a dielectric film on the substrate is obtained by a first parameter set calculation unit, a second parameter set calculation unit and a dielectric constant calculation unit, using the spectral reflectance and spectral transmittance of the substrate. It is thereby possible to achieve a noncontact measurement of the dielectric constant of the dielectric film on the substrate.

11 Claims, 4 Drawing Sheets

OTHER PUBLICATIONS

"Infared Switching Electrochromic Devices Based on Tungsten Oxide", Franke et al., J. App. Phys., vol. 88, No. 11 (2000), p. 1–7.

"Measurement of Rutile T102 Dielectric Tensor From 0.148 to 33um Using Generalized Ellipsometry", Tiwald et al., Proceeding of SPIE vol. 4103 (2000) p. 19–29.

"Dielectric Function of Amorphous Tantalum Oxide From the Far Infrared to the Deep Ultraviolet Spectral Region Measured by Spectroscopic Ellipsometry", Franke et al., J. App. Phys. vol. 88, No. 9, (2000) p. 1–9.

"Long–Wavelength Cutoff Filters of a New Type", Dobrowolski et al., App. Optics, vol. 38, No. 22, (1999) p. 4891–4903.

"Feasibility Study to Probe Thin Inorganic and Organic Coatings on Aluminum Substrates by Means of Visible and Infrared Spectroscopic ellipsometry", Schram et al., Surf. Interface Anal., 30, 507–513 (2000).

"Study of Surface Chemical Changes and Erosion Rates for CV–1144–0 Silicone Under Electron Cyclotron Resonance Oxygen Plasma Exposure", Yan et al., J. Vac. Sci. Technol. A 19(2) (2001) p. 447–454.

"Phase and Microstructure Investigations of Boron Nitride Thin Films by Spectroscopic Ellipsometry in the Visible and Infrared Spectral Range", Franke et al., J. App. Phys. 82(6) (1997) p. 2906–2911.

"Dielectric Function of Polycrystalline SiC from 190nm to 15um", Zollner et al., Phys. Stat. Sol. (B) 215, (1999) p. 21–25.

John A. Wooillam et al., "Overview of Variable Angle Spectroscopic Ellipsometry (VASE)," Part 1: Basic Theory and Typical Applications, SPIE Proc. vol. CR72 (1999) pp3–28 (English Translation of Japanese).

Blaine Johs et al. "Overview of Variable Angle Spectroscopic Ellipsometry (VASE)" Part 2; Advanced Applications, SPIE Proc. vol. CR72 (1999) pp29–58 (English Translation of Japanese).

Blaine Johs et al. "Characterization of Inhomogeneous and Absorbing Thin Films by Combined Spectroscopic Ellipsometry, Reflection, and Transmission Measurement ," Optical Interference Coatings Topical Meeting by Optical Society of America 1992 Technical Digest Series, vol. 15, Jun. 1–5, 1992, pp 433–436.

Michel Luttmann, "Infrared Spectroscopic Ellipsometry Devoted to Thin Film Characterization," Semiconductor Fabtech 6th Edition, May 1997, pp 387–391.

* cited by examiner

METHOD OF MEASURING DIELECTRIC CONSTANT USING LIGHT IN A PLURALITY OF WAVELENGTH RANGES

BACKGROUND OF THE INVENTION

1. Field of the Invention

The present invention relates to a method and an apparatus for performing a noncontact measurement of a dielectric constant of a dielectric film on a substrate.

2. Description of the Background Art

Conventionally, an oxide film ($SiO_2$) which is a dielectric thin film (hereinafter, referred to as "dielectric film") is formed on a semiconductor substrate (hereinafter, referred to as "substrate"), and the oxide film is used as an interlayer insulating film in an integrated circuit. With high integration of an LSI, recently, the problem of signal delay due to the characteristic of the dielectric film has become appreciable. In order to suppress the signal delay, a low dielectric-constant interlayer insulating film (hereinafter, referred to as "low dielectric constant film") is needed and various kinds of low dielectric constant films termed "low-k film" have been developed.

The low dielectric constant film has problems of unstable film quality, low resistance against etching gases and low mechanical strength, and the like, as compared with the conventional oxide film. Therefore, it is difficult to measure the dielectric constant of a low dielectric constant film by bringing a probe into contact therewith immediately after formation of the low dielectric constant film. In order to measure the dielectric constant of the low dielectric constant film, it is necessary to provide electrodes in the final step of an LSI manufacturing process and thereafter apply a voltage between the electrodes for the measurement.

In order to improve manufacturing yield of the LSI, however, it is preferable to measure and control the dielectric constant of the low dielectric constant film immediately after film formation, instead of measuring the dielectric constant after the final step in the manufacturing process.

SUMMARY OF THE INVENTION

The present invention is intended for a method of measuring a dielectric constant of a dielectric film on a substrate.

According to a first aspect of the present invention, the method comprises a first measurement step of acquiring reflectance, transmittance or an ellipsometry result at a plurality of wavelengths of light in a visible or near-ultraviolet wavelength range as a first optical characteristic of the substrate, a second measurement step of acquiring reflectance, transmittance or an ellipsometry result at a plurality of wavelengths of light in an infrared wavelength range as a second optical characteristic of the substrate, and a calculation step for obtaining the dielectric constant of the dielectric film using the first optical characteristic and the second optical characteristic.

The first aspect of the present invention makes it possible to perform a noncontact measurement of the dielectric constant of a dielectric film.

Preferably, the substrate is a semiconductor substrate, and the reflectance of the substrate in the visible or near-ultraviolet wavelength range is obtained as the first optical characteristic and the transmittance of the substrate in the infrared wavelength range is obtained as the second optical characteristic. Further preferably, the dielectric film is a low dielectric-constant interlayer insulating film formed on the substrate, and the visible or near-ultraviolet wavelength range includes a wavelength range ranging from 250 to 800 nm and the infrared wavelength range includes a wavelength range ranging from 2 to 40 $\mu$m.

According to a first preferable preferred embodiment, the dielectric constant is modeled by adding a constant term, the Sellmeier dispersion formula and the sum of the Lorenz oscillators in the calculation step, and the calculation step includes the steps of calculating values of the constant term and parameters in the Sellmeier dispersion formula on the basis of the first optical characteristic and calculating values of parameters of the Lorenz oscillators on the basis of the second optical characteristic.

The present invention is also intended for an apparatus for measuring a dielectric constant of a dielectric film on a substrate.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
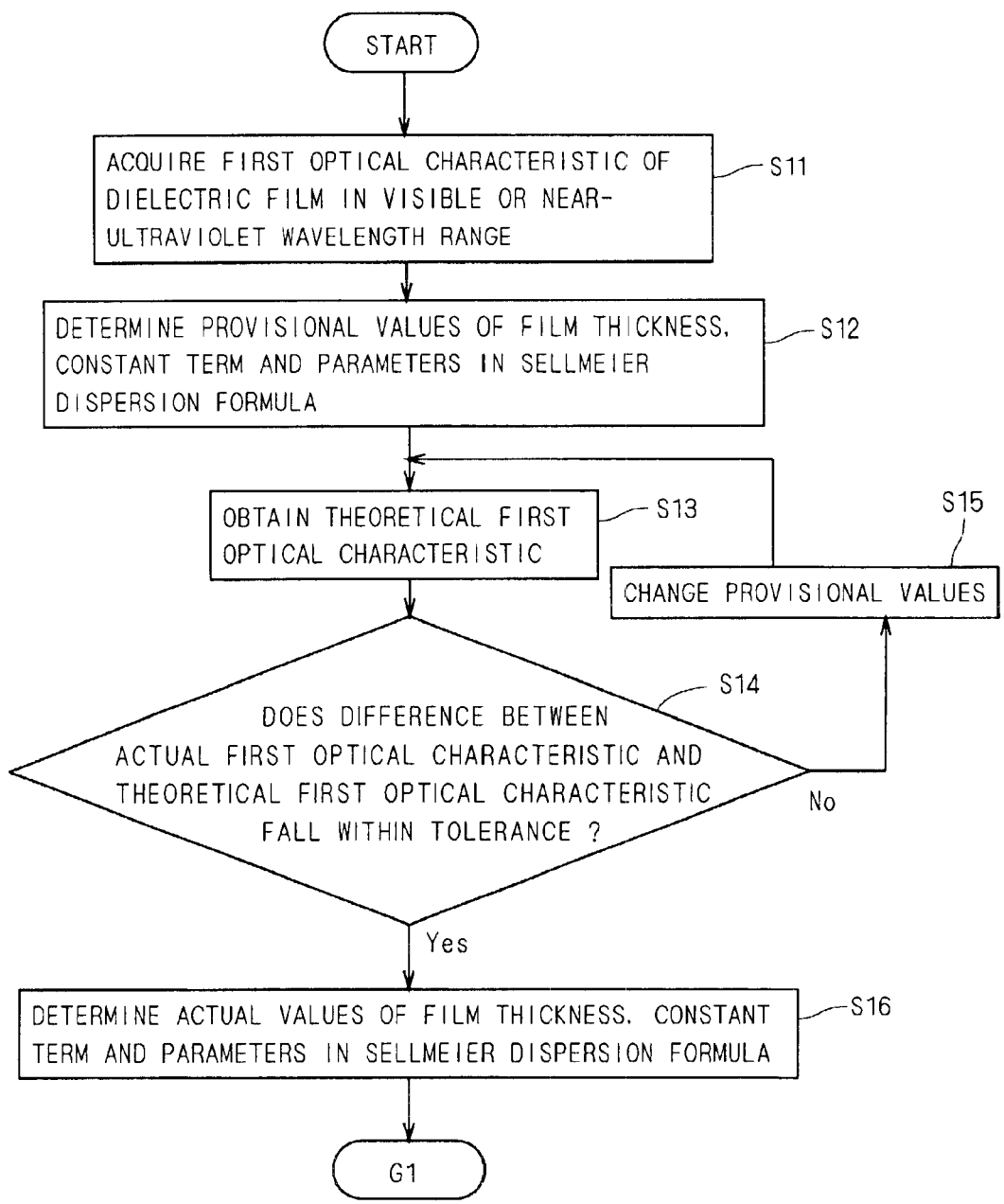
FIGS. 1 and 2 are flowcharts showing processes for obtaining the dielectric constant of a dielectric film.

<1. Principle and Method of Measuring Dielectric Constant>

From the dielectric constant (complex dielectric constant) at a certain wavelength (electromagnetic wave) of light and the film thickness of a dielectric film, the optical characteristics, such as reflectance, transmittance and complex reflectance ratio in the spectroscopic ellipsometry, of the dielectric film at the wavelength can be obtained. Conversely, assuming that the dielectric constant is a function of wavelength (where a real part and an imaginary part of the dielectric constant satisfy the Kramers-Kronig Dispersion relation, the function is hereinafter referred to as "model dielectric function"), the dielectric constant and the film thickness of the dielectric film can be obtained from the optical characteristics, such as reflectance, transmittance and complex reflectance ratio of the dielectric film at a plurality of wavelengths of light.

In the principle of measuring a dielectric constant, Eq. 1 is used as the model dielectric function;

$$\varepsilon(E) = \varepsilon_{1\infty} + \frac{AE_1^2}{E_1^2 - E^2} + \sum_n \frac{A_n E_{0n}^2}{E_{0n}^2 - E^2 + i\Gamma_n E_{0n} E} \quad (1)$$

The model dielectric function expressed by Eq. 1 is a function of energy E (=hv) and modeled as the sum of the first to third terms. The first term is a constant term $\varepsilon_{1\infty}$, the second term is the Sellmeier dispersion formula and the third term is the sum of the Lorenz oscillators, and the second and third terms model different kinds of polarizations in a dielectric film. In the second term, "A" represents an amplitude and "$E_1$" represents an energy of absorption peak out of measurement range. In the third term, "$A_n$" represents an amplitude of the n-th absorption peak, "$E_{On}$" represents Lorenz resonance frequency and "$\Gamma_n$" represents an extended parameter. Eq. 1 exactly satisfies the Kramers-Kronig dispersion relation.

In general, an insulating material consists of particles with positive electric charges such as nuclei and cations and particles with negative electric charges such as electrons and anions, and when an electric field is externally applied, opposite forces are given to these particles, to produce polarization. The dielectric constant refers to a physical quantity in macro understanding of polarization of a substance.

Polarizations of substances are broadly divided into three types, i.e., electronic polarization, ionic polarization and orientation polarization. The electronic polarization refers to a polarization caused by deviation in positional relation between the electron cloud and the nucleus of an atom in the electric field. The ionic polarization is caused by displacement of positive ions (cations) and negative ions (anions) in a crystal of ionic bond in the electric field. The orientation polarization is caused by orientation of molecules having permanent dipole moment to the direction of the electric field.

For example, the ionic polarization is dominant in sodium chloride (NaCl) and the orientation polarization is dominant in chlorine (HCl). Though a specific kind of polarization is ordinarily dominant thus, in general, the dielectric constant (i.e., polarization) is understood as the sum of effects of these polarizations.

These polarizations depend on the frequency of the electric field applied thereto. When the frequency of the electric field is increased, first, the orientation polarization can not follow the change of the electric field. This is because it takes time for molecules in liquid or solid to change their orientations. When the frequency of the electric field is further increased, the ionic polarization can not follow the change of the electric field in the frequency of an infrared region, and then the electronic polarization can not follow in the frequency of a visible or near-ultraviolet region. Such a frequency dependency of polarizations is termed dielectric dispersion.

In Eq. 1, the constant in the first term and the Sellmeier dispersion formula in the second term correspond to characteristics of a dielectric constant on the basis of the electronic polarization, and the sum of the Lorenz oscillators in the third term corresponds to a characteristic of the dielectric constant on the basis of the ionic polarization. Therefore, by irradiating a dielectric film to be measured with light in a visible or near-ultraviolet wavelength range and measuring the characteristic of the light led from the dielectric film, values of the constant in the first term and parameters in the Sellmeier dispersion formula in the second term can be obtained. After that, by irradiating the dielectric film with light in an infrared wavelength range and measuring the characteristic of the light led from the dielectric film, values of parameters of the Lorenz oscillators in the third term can be obtained.

Figure 2:
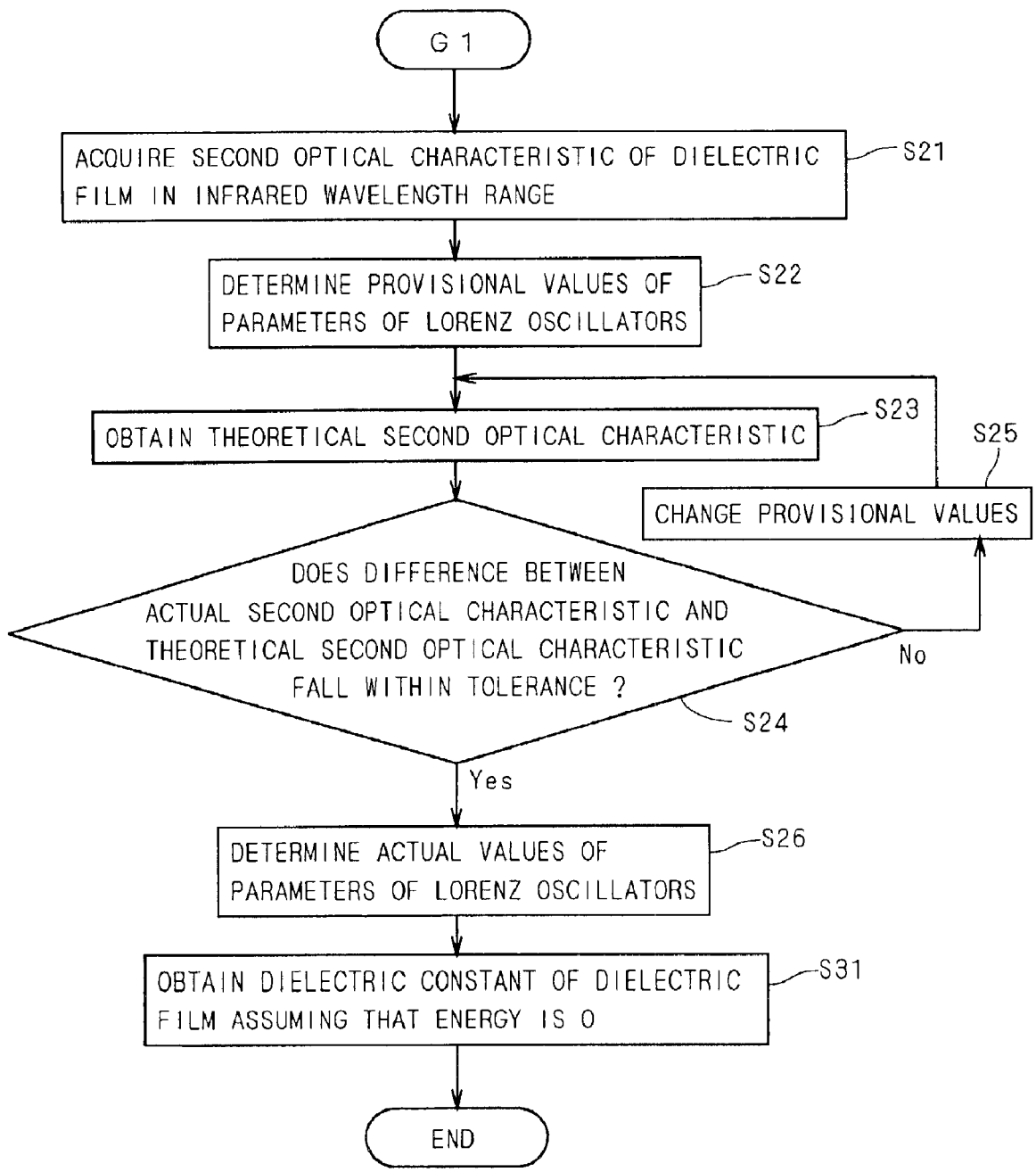

FIGS. 1 and 2 are flowcharts showing processes for obtaining a value of the constant term in the first term and values of parameters in the second and third terms of Eq. 1 by irradiating the dielectric film with light, and acquiring the dielectric constant of a dielectric film.

First, the (spectral) reflectance, transmittance or ellipsometry result (complex reflectance ratio in an ellipsometry (the ratio between the major axis and the minor axis of an elliptically polarized light and the phase shift between an electric field and a magnetic field)) of a dielectric film at a plurality of wavelengths of light in a visible or near-ultraviolet wavelength range is measured as the first optical characteristic of the dielectric film (Step S11). The reflectance and the transmittance at a plurality of wavelengths can be acquired at once with a spectrophotometer and the complex reflectance ratio at a plurality of wavelengths can be acquired at once with a spectroellipsometer.

Next, a provisional film thickness T of the dielectric film and provisional values of the constant term $\in_{1\infty}$ in the first term and the parameters A and $E_1$ in the second term of Eq. 1 are determined (Step S12), and a theoretical first optical characteristic is obtained from these provisional values (Step S13). At that time, among the theoretical reflectance, transmittance and complex reflectance ratio, the same kind of first optical characteristic as actually measured is obtained. An approximate value of the film thickness T can be determined from a condition of film formation, and approximate values of the constant term $\in_{1\infty}$ and the parameters A and $E_1$ can be also determined from the material of the dielectric film. Therefore, such estimation values are determined as initial values.

After obtaining the theoretical first optical characteristic, the actual first optical characteristic obtained by the measurement in Step S11 and the theoretical first optical characteristic are compared with each other, and it is checked whether the difference between these two optical characteristics falls within tolerance or not (Step S14). Usually, since the actual first optical characteristic and the theoretical first optical characteristic are different from each other in the first comparison, the theoretical first optical characteristic is obtained again by slightly changing the provisional values of the film thickness T, the constant term $\in_{1\infty}$ and the parameters A and $E_1$ (Steps S15 and S13).

After that, the change of the provisional values of the film thickness T, the constant term $\in_{1\infty}$ and the parameters A and $E_1$ and calculation of the theoretical first optical characteristic are repeated by using a nonlinear optimization method such as a simplex method or a least squares method until the difference between the actual first optical characteristic and the theoretical first optical characteristic falls within tolerance (Steps S13 to S15). When the difference between these first optical characteristics falls within tolerance, the values of the film thickness T, the constant term $\in_{1\infty}$ and the parameters A and $E_1$ at this time are determined as actual values (Step S16).

Subsequently, the (spectral) reflectance, transmittance or complex reflectance ratio of the dielectric film at a plurality of wavelengths of light in an infrared wavelength range is measured as the second optical characteristic of the dielectric film (Step S21). These optical characteristics at a plurality of wavelengths can be acquired at once with the spectrophotometer and the spectroellipsometer.

Next, provisional values of the parameters $A_n$, $E_{on}$ and $\Gamma_n$ in the third term of Eq. 1 are determined, and the theoretical second optical characteristic is obtained by using the values of the film thickness T, the constant term $\in_{1\infty}$ and the parameters A and $E_1$ which are determined in Step S15 (Steps S22 and S23). At that time, among the theoretical reflectance, transmittance and complex reflectance ratio, the same kind of second optical characteristic as actually measured is obtained. Approximate values of the parameters $A_n$, $E_{on}$ and $\Gamma_n$ can be determined from the material of the dielectric film.

After that, like in the case of the first optical characteristic, the actual second optical characteristic obtained by the measurement in Step S21 and the theoretical second optical characteristic obtained in Step S22 are compared with each other, and the change of the provisional values of the parameters $A_n$, $E_{on}$ and $\Gamma_n$ and calculation of the theoretical second optical characteristic are repeated until the difference between these second optical characteristics falls within tolerance (Steps S23 to S25).

When the difference between the actual second optical characteristic and the theoretical second optical characteristic falls within tolerance, the values of the parameters $A_n$, $E_{on}$ and $\Gamma_n$ at this time are determined as actual values (Step S26).

After obtaining the values of the constant term and the parameters in Eq. 1, by substituting zero into the energy E, $\in(0)$ is determined as the dielectric constant to be obtained (Step S31). This is because the frequency of electric field while the dielectric film is used as part of an electric circuit is sufficiently smaller than the frequency of electric field caused by the light, there is a high correlation between the electric dielectric constant and the optical dielectric constant, and the static dielectric constant where the energy E (=hv) of change of electric field assumed to be zero is adoptable as the dielectric constant of the dielectric film. In other words, the dielectric constant of the dielectric film can be obtained as Eq. 2:

$$\varepsilon(0) = \varepsilon_{1\infty} + A + \sum_n A_n \quad (2)$$

Through the above process, it is possible to measure the electric dielectric constant of a dielectric film by a noncontact optical method. Further, since the degree of effects of the ionic polarization and the electronic polarization on the dielectric constant can be quantitatively obtained by the above method, a higher-level analysis can be achieved on a dielectric film.

Step S21 may be executed before Steps S12 to S16 (or in parallel) or before Step S11.

<2. Exemplary Constitution of Apparatus>

Figure 3:
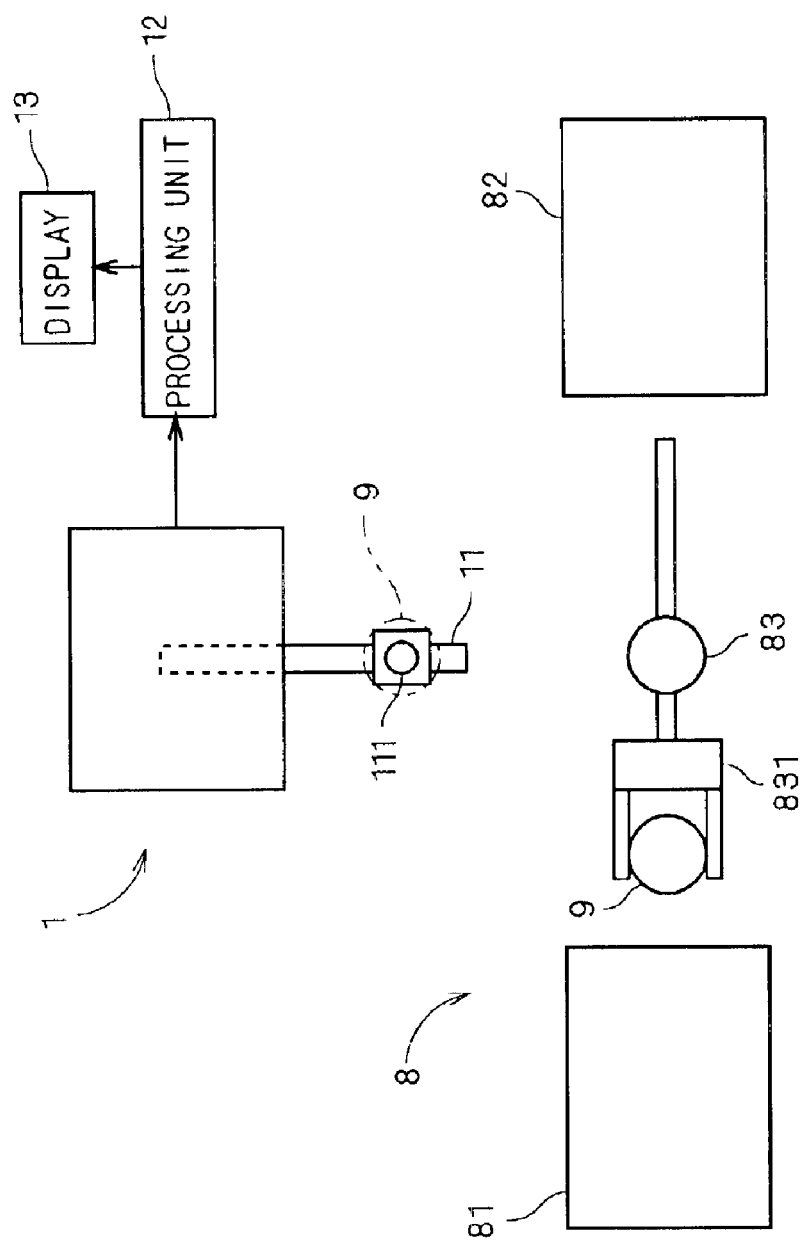
FIG. 3 is a view showing an exemplary use of a dielectric constant measuring apparatus.

FIG. 3 is a view showing an exemplary constitution of a dielectric constant measuring apparatus 1 for achieving the above-discussed method of measuring a dielectric constant.

The dielectric constant measuring apparatus 1 is incorporated in a manufacturing line 8 for manufacturing a semiconductor substrate 9. Though it is possible to use the dielectric constant measuring apparatus 1 independently, since a noncontact measurement is possible, an in-line measurement of the dielectric constant can be performed even if the dielectric film to be measured has low mechanical strength, such as an interlayer insulating film of low dielectric constant (low dielectric constant film). FIG. 3 shows only a film formation apparatus 81 on the upstream side and a coating apparatus 82 on the downstream side, as examples, in the manufacturing line 8.

Between the film formation apparatus 81 and the coating apparatus 82, a transfer robot 83 for transferring the substrate 9 is arranged. The transfer robot 83 has a hand 831 for rotation and sliding movement. On the other hand, the dielectric constant measuring apparatus 1 has a transport robot 11 for transporting the substrate 9 into the apparatus by chucking the substrate 9 with en a vacuum chucking head 111.

The transfer robot 83 takes the substrates 9 out of the film formation apparatus 81 and transfers the same to the coating apparatus 82 and to the transport robot 11 of the dielectric constant measuring apparatus 1 once in several substrates to several tens. In other words, the transfer robot 83 transfers the substrates 9 between the manufacturing line 8 and the dielectric constant measuring apparatus 1. The transport robot 11 transports the substrate 9 into the inside of the dielectric constant measuring apparatus 1 and takes the substrate 9 after measurement out of the dielectric constant measuring apparatus 1 and transports the same to the transfer robot 83. All the substrates 9 may be transported to the dielectric constant measuring apparatus 1.

The dielectric constant measuring apparatus 1 irradiates the substrate 9 with light in a visible or near-ultraviolet wavelength range and light in an infrared wavelength range, and transfers obtained data to a processing unit 12. The processing unit 12 performs the above calculation and the obtained dielectric constant is displayed on a display 13.

Figure 4:
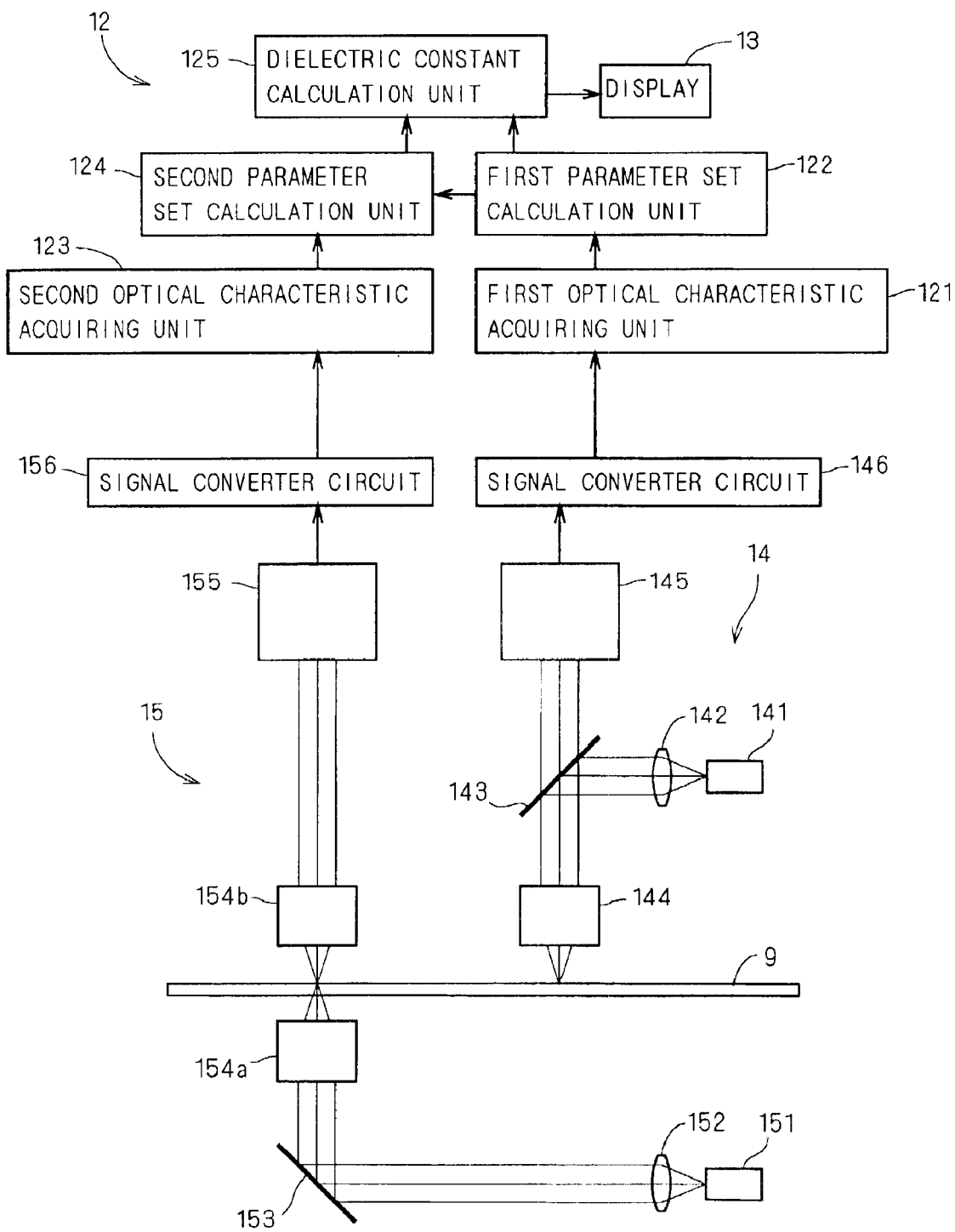
FIG. 4 is a view showing an internal constitution of the dielectric constant measuring apparatus and functions of a processing unit.

FIG. 4 is a view showing an internal constitution of the dielectric constant measuring apparatus 1 and functions of the processing unit 12. In FIG. 4, a first optical characteristic acquiring unit 121, a first parameter set calculation unit 122, a second optical characteristic acquiring unit 123, a second parameter set calculation unit 124 and a dielectric constant calculation unit 125 are functions of the processing unit 12. These functions are achieved by performing computation with a CPU according to a predetermined program, and how to divide these functions may be arbitrarily changed. Furthermore, each function may be performed by a dedicated electric circuit, and in this case, it is not necessary that each function is definitely formed as a circuit.

In the inside of the dielectric constant measuring apparatus 1 arranged are a first optical system 14 for irradiating the substrate 9 with light in the visible or near-ultraviolet wavelength range and receiving light from the substrate 9 and a second optical system 15 for irradiating the substrate 9 with light in the infrared wavelength range and receiving light from the substrate 9.

The first optical system 14 is provided with a light source 141 for emitting the light in the visible or near-ultraviolet wavelength range, and the light from the light source 141, being condensed on the substrate 9 through a lens 142, a half mirror 143 and a condensing lens 144, is perpendicularly applied to the substrate 9. The light reflected on the substrate 9 is led again to the condensing lens 144, going through the half mirror 143, enters a spectroscope 145 and is received thereby. Specifically, the reflected light from the substrate 9 is dispersed by the grating in the spectroscope 145 and led to a light receiving element array, and light components thereof are received in the light receiving element array by wavelengths. An output from the spectroscope 145 is converted into digital data by a signal converter circuit 146 and the first optical characteristic acquiring unit 121 acquires the spectral reflectance of the substrate 9 on the basis of the digital data outputted from the signal converter circuit 146.

On the other hand, the second optical system 15 is provided with a light source 151 for emitting the light in the infrared wavelength range, and the light from the light source 151, being condensed on a lower surface of the substrate 9 through a lens 152, a half mirror 153 and a condensing lens 154a, is applied to the substrate 9. The infrared light goes from the lower side to the upper side of the substrate 9 and the transmission light enters a spectroscope 155 through an objective lens 154b and is received thereby. An output from the spectroscope 155 is converted into digital data by a signal converter circuit 156 and the second optical characteristic acquiring unit 123 acquires the spectral transmittance of the substrate 9 on the basis of the digital data outputted from the signal converter circuit 156.

Through the above-discussed operation, the spectral reflectance on the visible or near-ultraviolet wavelength range is acquired as the first optical characteristic of the substrate 9 on which a dielectric film is formed and the spectral transmittance on the infrared wavelength range is acquired as the second optical characteristic. These operations correspond to Step S11 of FIG. 1 and Step S21 of FIG. 2.

A mount supporting the substrate 9 in the dielectric constant measuring apparatus 1 is horizontally movable, and the spectral reflectance and the spectral transmittance are measured on the same portion of the substrate 9.

After that, Steps S12 to S16 are executed by the first parameter set calculation unit 122, to obtain the values of the film thickness T and the parameters in the Sellmeier dispersion formula. Further, the values of the film thickness and the parameters are inputted to the second parameter set calculation unit 124 and Steps S22 to S26 are executed therein, to obtain the values of the parameters of the Lorenz oscillators.

Finally, the dielectric constant calculation unit 125 executes Step S31. Specifically, the dielectric constant of the dielectric film is obtained from Eq. 2. The obtained dielectric constant is displayed on the display 13 and notified to an operator. Further, the substrate 9 is horizontally moved as required and the dielectric constant of other portions of the substrate 9 is measured.

<3. Other Method of Acquiring Optical Characteristic and Experimental Result>

Though the dielectric constant measuring apparatus 1 acquires the spectral reflectance as the first optical characteristic of the substrate 9 and the spectral transmittance as the second optical characteristic, these optical characteristics may be any one of the reflectance and the transmittance at perpendicular incidence and the complex reflectance ratio in the ellipsometry at diagonal incidence at a plurality of wavelengths of light. This is because these optical characteristics can be theoretically obtained from the values of the film thickness and the parameters and used as in the above method.

Though a spectrophotometer may be used for the measurement of reflectance and transmittance, optical instruments to acquire only the reflectance or the transmittance at a plurality of specific wavelengths may be used. Further, for acquisition of the second optical characteristic using the infrared light, a transmission-type or reflection-type FT-IR device (using the Fourier transform infrared spectroscopy) may be used. In the case of using the complex reflectance ratio, an spectroellipsometer can be used. Since the complex reflectance ratio has two components, by using the spectroellipsometer, it is possible to measure the dielectric constant with high accuracy. The above optical instruments may be arbitrarily incorporated in the dielectric constant measuring apparatus 1, and for example, the spectroellipsometer and the FT-IR device may be incorporated therein.

The dielectric constant measuring apparatus 1, which can perform a noncontact and nondestructive measurement of the dielectric constant of a dielectric film on the substrate 9, is particularly suitable for measurement on a low dielectric constant film (low-k film) having low mechanical strength. In this case, it is preferable, in view of the material of low dielectric constant, that the visible or near-ultraviolet wavelength range includes the wavelength range ranging from 250 to 800 nm and it is preferable, in consideration of frequency range of molecular vibration, that the infrared wavelength range includes the wavelength range ranging from 2 to 40 $\mu$m.

Table 1 shows a result of measurement on dielectric constants of low dielectric constant films using the light in these wavelength ranges. The measurement result of Table 1 shows the dielectric constants obtained on the basis of the complex reflectance ratio acquired as the first optical characteristic by a spectroellipsometer using the light in the visible or near-ultraviolet wavelength range and the spectral transmittance acquired as the second optical characteristic by the FT-IR device using the light in the infrared wavelength range.

TABLE 1

| Types of Low Dielectric Constant Film | Dielectric Constant Presented by Maker | Dielectric Constant by Measurement |
| --- | --- | --- |
| Type 1 | 2.8 | 2.78 |
| Type 2 | 2.5 | 2.57 |
| Type 3 | 2.65 | 2.66 |

As shown in Table 1, by using the two optical characteristics in the predetermined wavelength ranges, it is possible to obtain the dielectric constants of three types of dielectric films with high accuracy.

Since a semiconductor substrate is opaque for the light in the visible or near-ultraviolet wavelength range and transparent for the light in the infrared wavelength range, in the case of semiconductor substrate, it is possible to easily measure the dielectric constant by acquiring the reflectance at a plurality of wavelengths of light as the first optical characteristic and the transmittance at a plurality of wavelengths as the second optical characteristic. In a case where interconnection is formed on the semiconductor substrate, however, it is preferable that the reflectance at a plurality of wavelengths should be acquired as the second optical characteristic.

The substrate may be a glass substrate. In this case, since the substrate is transparent for the light in the visible or near-ultraviolet wavelength range and opaque for the light in the infrared wavelength range, it is preferable that the transmittance at a plurality of wavelengths should be acquired as the first optical characteristic and the spectral reflectance at a plurality of wavelengths should be acquired as the second optical characteristic in measuring the dielectric constant.

Further, two or more may be acquired out of the reflectance, the transmittance and the complex reflectance ratio as the first and second optical characteristics. The absorptivity of the film-formed substrate may be obtained as optical characteristic, and the measurement of the absorptivity is the same as use of the reflectance and the transmittance. When the reflectance is extremely small, particularly, using the absorptivity is equivalent to using the transmittance.

<4. Variations>

Though the preferred embodiment of the present invention has been discussed above, the present invention is not limited to the above-discussed preferred embodiment, and various variations are possible.

For example, though the dielectric constant measuring apparatus 1 are provided with the first optical system 14 and the second optical system 15 for irradiating the substrate 9 with two kinds of light, respectively, all of or part of these optical systems may be shared.

Conversely, the first optical system 14 and the second optical system 15 may be provided as individual devices. The processing unit 12 may be also provided as an individual computer and connected to the dielectric constant measuring apparatus 1.

As the model dielectric function used in the above preferred embodiment, other functions may be used. Parameter values in the modeled function may be obtained by other methods.

While the invention has been shown and described in detail, the foregoing description is in all aspects illustrative and not restrictive. It is therefore understood that numerous modifications and variations can be devised without departing from the scope of the invention.

What is claimed is:

1. A method of measuring a dielectric constant of a dielectric film on a substrate, comprising:
   a first measurement step of acquiring reflectance, transmittance or an ellipsometry result at a plurality of wavelengths of light in a visible or near-ultraviolet wavelength range as a first optical characteristic of said substrate;
   a second measurement step of acquiring reflectance, transmittance or an ellipsometry result at a plurality of wavelengths of light in an infrared wavelength range as a second optical characteristic of said substrate; and
   a calculation step for obtaining said dielectric constant of said dielectric film using said first optical characteristic and said second optical characteristic.

2. The method according to claim 1, wherein
   said substrate is a semiconductor substrate, and
   said reflectance of said substrate in said visible or near-ultraviolet wavelength range is obtained as said first optical characteristic and said transmittance of said substrate in said infrared wavelength range is obtained as said second optical characteristic.

3. The method according to claim 2, wherein
   said dielectric film is a low dielectric-constant interlayer insulating film formed on said substrate.

4. The method according to claim 3, wherein
   said visible or near-ultraviolet wavelength range includes a wavelength range ranging from 250 to 800 nm and said infrared wavelength range includes a wavelength range ranging from 2 to 40 $\mu$m.

5. The method according to claim 1, wherein
   said dielectric constant is modeled by adding a constant term, the Sellmeier dispersion formula and the sum of the Lorenz oscillators in said calculation step, and
   said calculation step includes the steps of:
   calculating values of said constant term and parameters in said Sellmeier dispersion formula on the basis of said first optical characteristic; and
   calculating values of parameters of said Lorenz oscillators on the basis of said second optical characteristic.

6. An apparatus of measuring a dielectric constant of a dielectric film on a substrate, comprising:
   a first light source for emitting first light in a visible or near-ultraviolet wavelength range with which said substrate is irradiated;
   a first light receiving unit for receiving light led from said substrate by irradiation with said first light;
   a second light source for emitting second light in an infrared wavelength range with which said substrate is irradiated;
   a second light receiving unit for receiving light led from said substrate by irradiation with said second light; and
   an operation unit for obtaining reflectance, transmittance or an ellipsometry result at a plurality of wavelengths of said first light as a first optical characteristic of said substrate on the basis of an output of said first light receiving unit, obtaining reflectance, transmittance or an ellipsometry result at a plurality of wavelengths of said second light as a second optical characteristic of said substrate on the basis of an output of said second light receiving unit, and obtaining said dielectric constant of said dielectric film using said first optical characteristic and said second optical characteristic.

7. The apparatus according to claim 6, further comprising:
   a transfer system for transferring said substrate to/from a manufacturing line of said substrate.

8. The apparatus according to claim 6, wherein
   said substrate is a semiconductor substrate, and
   said reflectance of said substrate in said visible or near-ultraviolet wavelength range is obtained as said first optical characteristic and said transmittance of said substrate in said infrared wavelength range is obtained as said second optical characteristic.

9. The apparatus according to claim 8, wherein
   said dielectric film is a low dielectric-constant interlayer insulating film formed on said substrate.

10. The apparatus according to claim 9, wherein
    said visible or near-ultraviolet wavelength range includes a wavelength range ranging from 250 to 800 nm and said infrared wavelength range includes a wavelength range ranging from 2 to 40 $\mu$m.

11. The apparatus according to claim 6, wherein
    said dielectric constant is modeled by adding a constant term, the Sellmeier dispersion formula and the sum of the Lorenz oscillators in said operation unit, and
    said operation unit calculates values of said constant term and parameters in said Sellmeier dispersion formula on the basis of said first optical characteristic and values of parameters of said Lorenz oscillators on the basis of said second optical characteristic.

* * * * *